US007375829B2

(12) United States Patent
Kang

(10) Patent No.: US 7,375,829 B2
(45) Date of Patent: May 20, 2008

(54) METHOD FOR INSPECTING AN INSULATOR WITH A LIBRARY OF OPTIC IMAGES

(75) Inventor: Jung Ho Kang, Gyeonggi-do (KR)

(73) Assignee: Dongbu Electronics Co., Ltd., Seoul (KR)

( * ) Notice: Subject to any disclaimer, the term of this patent is extended or adjusted under 35 U.S.C. 154(b) by 356 days.

(21) Appl. No.: 10/756,770

(22) Filed: Jan. 14, 2004

(65) Prior Publication Data
US 2005/0018210 A1 Jan. 27, 2005

(30) Foreign Application Priority Data
Jul. 21, 2003 (KR) .................. 10-2003-0049615

(51) Int. Cl.
G01B 11/28 (2006.01)
G01N 21/00 (2006.01)
G01N 21/86 (2006.01)
G06K 9/00 (2006.01)
G01V 8/00 (2006.01)

(52) U.S. Cl. ................ 356/630; 356/237.4; 356/237.5; 382/145; 382/149; 250/559.27

(58) Field of Classification Search ...................... None
See application file for complete search history.

(56) References Cited

U.S. PATENT DOCUMENTS 5,365,340 A    11/1994 Ledger
5,436,725 A *  7/1995  Ledger ...................... 356/504
5,899,792 A *  5/1999  Yagi ............................ 451/6
5,964,643 A    10/1999 Birang et al.
6,128,403 A *  10/2000 Ozaki ......................... 382/145
6,512,842 B1 * 1/2003  Steffan et al. .............. 382/149

(Continued)

FOREIGN PATENT DOCUMENTS

KR    1020010029984    4/2001

OTHER PUBLICATIONS

Abstract and Figure Korean Patent, KR 2001001224 A, of Seo, S. R. published Jan. 5, 2001.*

Primary Examiner—Gregory J. Toatley, Jr.
Assistant Examiner—Gordon J. Stock, Jr.
(74) Attorney, Agent, or Firm—Pillsbury Winthrop Shaw Pittman LLP

(57) ABSTRACT

A method for inspecting an insulator with a library of optic images is disclosed. The method for inspecting an insulating layer according to the present invention, comprises the steps of collecting standard data for thickness of the insulating layer; collecting standard data for an optic image of the insulating layer; making a library by matching standard data for the thickness and the optic image; and inspecting the insulating layer with the library. Thus, the method of inspecting an insulating layer by using the thickness and the library of optic images in the present invention can considerably improve the conventional methods that depend only on the thickness or the optic images by making the thickness and the optic image for the part or whole of the wafer into a form of data, matching them, and making a library of them. Because the lack of wafer representative due to the restriction of monitoring pattern is overcome and the wafer representative is improved, monitoring the process and measuring the global planarization for wafer unit can be more accurate.

6 Claims, 2 Drawing Sheets

U.S. PATENT DOCUMENTS

| | | | |
|---|---|---|---|
| 6,744,266 B2 * | 6/2004 | Dor et al. | 324/751 |
| 6,753,972 B1 * | 6/2004 | Hirose et al. | 356/630 |
| 6,815,947 B2 * | 11/2004 | Scheiner et al. | 324/230 |
| 7,068,363 B2 * | 6/2006 | Bevis et al. | 356/237.5 |
| 7,095,511 B2 * | 8/2006 | Chalmers et al. | 356/630 |
| 2002/0072133 A1 | 6/2002 | Jun et al. | |
| 2005/0046850 A1 * | 3/2005 | Chow | 356/430 |
| 2006/0219678 A1 * | 10/2006 | Sopori | 219/121.72 |

* cited by examiner

Field Oxide

Field Oxide

METHOD FOR INSPECTING AN INSULATOR WITH A LIBRARY OF OPTIC IMAGES

CROSS REFERENCE TO RELATED APPLICATIONS

This application claims priority to Korean Patent Application No. 10-2003-0049615, filed on Jul. 21, 2003.

BACKGROUND OF THE INVENTION

1. Field of the Invention

The present invention relates to a method for inspecting an insulator with a library of optic images and, more particularly, to a method for monitoring a uniformity of STI Shallow Trench Isolation) in CMP (Chemical Mechanical Polishing) process in the fabrication process of semiconductor device.

2. Background of the Related Art

When a fault occurs for the pattern of a middle process during fabrication process of semiconductor device, yield of the device decreases. Therefore, methods of inspecting the pattern in the middle process of the fabrication process are being vigorously studied. Such methods include systems and methods based on the identification of a visible pattern fault in the optic image of a wafer, that is, the comparison of features between a basic image and a test image. The features include size, shape, average pixel strength, a center of gravity, diameter, region, and a variance.

For example, a conventional method is based on a voltage-contrast image of a wafer with a scanning electronic beam. The method which inspects faults from the voltage-contrast image is based on the difference of pixel-strength values between an image of a pattern to inspect and the basic image. To extract the faults, these two images or image regions are corrected for the differences in the brightness and the contrast and then arranged. Next, the difference image is made by obtaining the difference of the pixel-strength value for each pixel. By determining a boundary value in the difference image, a fault image is made such that the pixel value becomes binary. The characteristics in the fault image that satisfy particular states such as minimum size, shape, and strength are regarded as faults. Then, statistics of the faults in the images are calculated and reported. For instance, the most serious fault and the number of faults are repeated for each image. As the most serious fault is first handled and analyzed in reviewing the images based on these statistics, reviewing time is considerably diminished. An advantage of this method lies in that it does not require the electrical features or the knowledge of the structure in the voltage-contrast images, and just the alignment and the image normalization can correct the total difference within the images or the image regions. Thus, without the electrical pattern being inspected in advance, the voltage-contrast fault can be detected in this method.

However, the weak point of the above method is that any image difference is regarded as a potential fault. So, it is difficult to tell the difference between an obvious fault and an unnecessary fault which is actually not a fault, but an insignificant error on the surface or artificial objects for images. Several artificial objects in the inspection procedure cause an image alignment error, a local image distortion, and nonlinearity in scanning process for obtaining a voltage-contrast image. The obvious faults occur so rare in general that the number of the unnecessary faults can be much more than that of the obvious faults. More than 90% of reported faults can be classified into the unnecessary faults in conventional pixel-substrate inspection system. To separate the unnecessary faults from the obvious faults require much time and endeavor by a man. The high proportion of the unnecessary faults and the requirement of inspection by a man make it difficult to improve the performance of an inspection processor, the usage of which becomes more frequent in the fabrication of a semiconductor wafer. To decrease the proportion of the unnecessary faults due to the alignment error, the conventional solutions such as a precise wafer-stage positioning, uniform and reproducible imaging, and an improved fault-detection algorithm require many processes, mcuh time, and many hardware devices.

On the other hand, a method for maintaining a planarization of insulating layer, which measures only thickness of monitoring pattern, also has a limitation to gather data all over the inspection range and a restriction on the size and the location of the monitoring pattern. So it may not represent the degree of uniformity of the fine circuit inside a chip. Moreover, as the line width of a circuit gets gradually thinner, the feature of the monitoring pattern as a chip representative gets more dilute. Thus, the maintenance of the planarization of the insulating layer only by the conventional thickness measurement is practically faced with the limit.

U.S. Pat. No. 5,964,643 discloses apparatus and method for in-situ monitoring of chemical mechanical polishing operations. An in-situ method of measuring uniformity of a layer on a substrate during polishing of said layer, where the method includes the steps of directing a light beam toward the layer during polishing; monitoring an interference signal produced by the light beam reflecting off of the substrate; and computing a measure of uniformity from the interference signal.

U.S. Pat. No. 5,365,340 discloses apparatus and method for measuring the thickness of thin films. A measurement instrument which detects the thickness of the outer layer of a wafer, includes a filtered white light source forming an aperture image. The white light source includes a halogen lamp, a condensing lens, a circular aperture, a collimator lens, a narrow band filter wheel, and a second collimator lens. A monochromatic beam generated by this filtered white light source illuminates the entire surface of the wafer with collimated light that has passed through a third collimator lens. The light reflected off the wafer returns through the third collimator lens and forms an aperture image upon an optical device which redirects this image to a charge coupled device (CCD) camera. The image is converted to a map of measured reflectance data by a digitizing circuit and a computer. This map of measured reflectance data is then self-normalized and compared to reference reflectance data to generate a map of the outer layer thickness profile of the wafer.

U.S. Published Patent No. 2002-0072133 discloses a method and apparatus for numerically analyzing a growth degree of grains grown on a surface of a semiconductor wafer. A method and apparatus for numerically analyzing a growth degree of grains grown on a surface of a semiconductor wafer, in which the growth degree of grains is automatically calculated and numerated through a computer by using an image file of the surface of the semiconductor wafer scanned by an SEM. A predetermined portion of a surface of the wafer is scanned using the SEM, and the scanned SEM image is simultaneously stored into a database. An automatic numerical program applies meshes to an analysis screen frame and selects an analysis area on a measured image. Thereafter, a smoothing process for reducing an influence of noise is performed on respective pixels designated by the meshes using an average value of image data of adjacent pixels. A standardization process is then performed, based on respective images in order to remove a brightness difference between the measured images. After comparing standardized image data values of the respective pixels with a predetermined threshold value, the number of pixels whose standardized image data value is greater than the threshold value is counted. The growth degree of grains on the surface of the wafer is calculated by numerating a ratio of the counted number with respect to a total number of the pixels contained within the analysis target image.

BRIEF DESCRIPTION OF THE DRAWINGS

The accompanying drawings, which are included to provide a further understanding of the invention and are incorporated in and constitute a part of this application, illustrate embodiment of the invention and together with the description serve to explain the principle of the invention. In the drawings.

DETAILED DESCRIPTION OF THE PREFERRED EMBODIMENT

The present invention is directed to a method for inspecting an insulator with a library of optic images that substantially obviates one or more problems due to limitations and disadvantages of the related art.

An object of the present invention is to provide a method for inspecting an insulator with a library of optic images by which the uniformity of the insulating layer is monitored quickly and accurately by collecting data for thickness and optic images of permeable insulating layer deposited or planarized on a substrate.

To achieve the object, the present invention provides a method for inspecting an insulator deposited or planarized on a substrate in fabrication processes of semiconductor with a library of optic images, the method comprising the steps of:

collecting standard data for thickness of the insulating layer;

collecting standard data for an optic image of the insulating layer;

making a library by matching standard data for the thickness and the optic image; and inspecting the insulating layer with the library.

Reference will now be made in detail to the preferred embodiments of the present invention, examples of which are illustrated in the accompanying drawings.

STI process comprises the following steps of: depositing and patterning an oxide layer and a nitride layer on a semiconductor substrate; forming a trench by etching the substrate; forming a thin film on the trench; performing a cleaning process; forming an STI oxide layer; performing a mot etching clearing process to remove impurities in the film and an annealing process for a stability of the film; and performing a CMP process.

Figure 1:
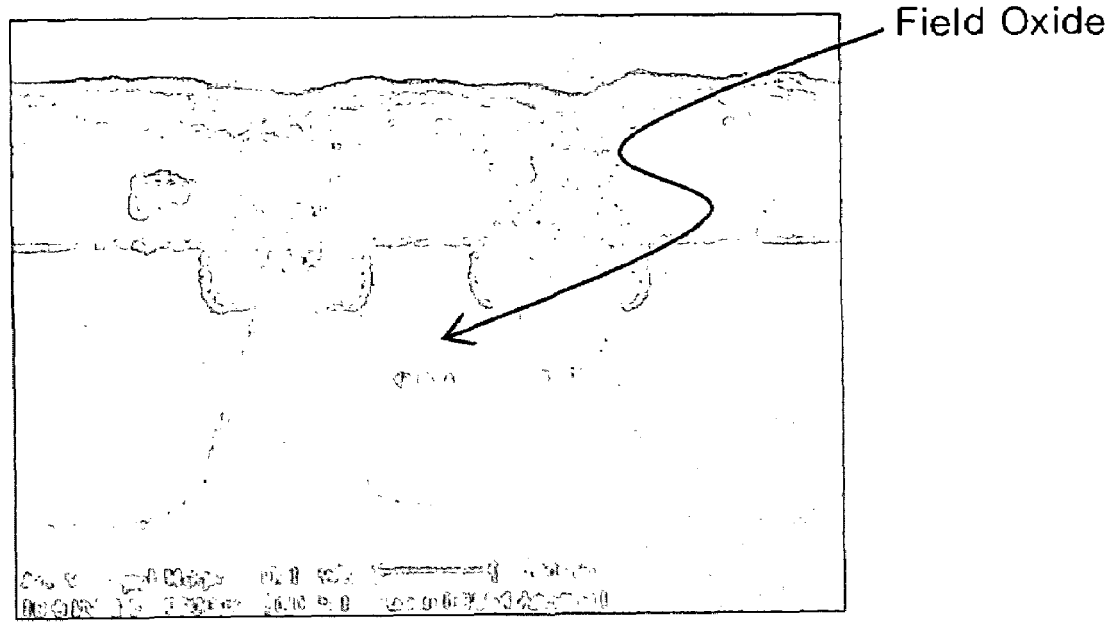
FIG. 1 is a photograph illustrating, in a vertical cross-sectional view, a section by STI CMP.

FIG. 1 illustrates, in a vertical cross-sectional view, a section by STI CMP. The location of the STI oxide layer is shown. First, standard thickness of a monitoring pattern is made into a form of data. In collecting data for thickness, it is important to collect data of the important location of the pattern, for example, boundary of the STI oxide layer, although collecting data of the whole pattern is also possible.

The thickness data can be collected for a particular region as in the described method or for the whole. The equipments for measuring the thickness are a nanometer, an ellipsometer, etc. The principle of these equipments is counting of thickness according to the difference in the reflection rate between a deposited oxide layer and a lower layer thereof.

Figure 2:
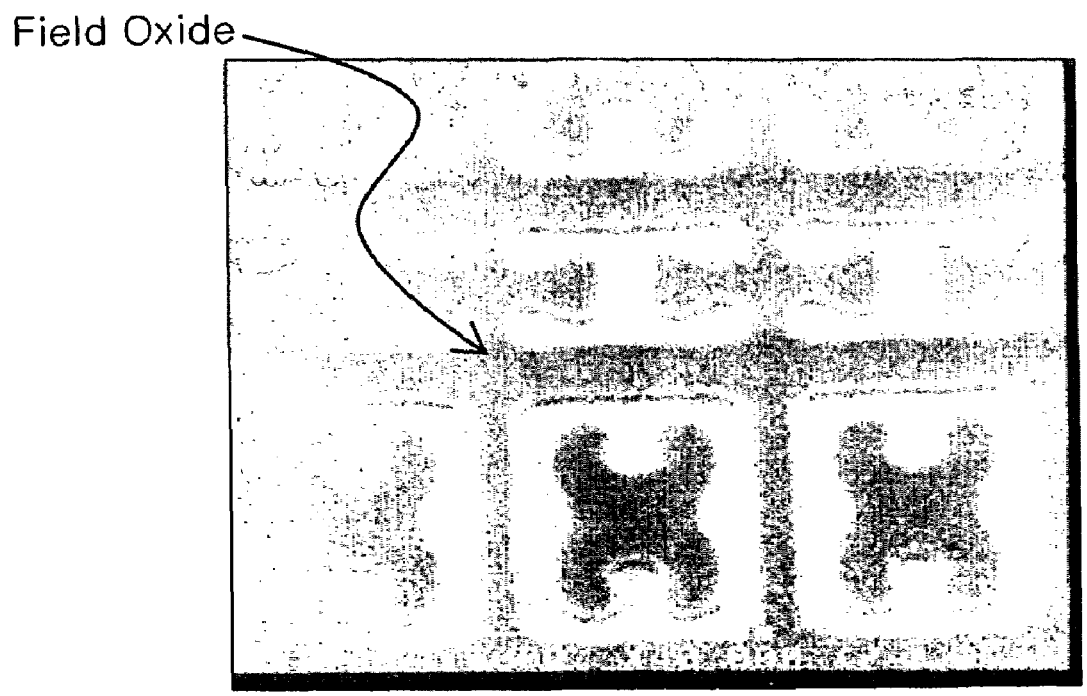
FIG. 2 illustrates, in a plane view, the substrate of FIG. 1.

FIG. 2 illustrates, in a plane view, the substrate of FIG. 1, and indicates the location of the STI oxide layer for an example to get an optic image corresponding to the standard thickness data from a monitoring pattern like FIG. 1. As shown in FIGS. 1 and 2, it is confirmed that the degree of protrusion or sinking of the oxide layer on the STI region is very large. Because such protrusion or sinking always exists, using the thickness and the optic image simultaneously provides a more accurate and quick inspection than using just one of them.

Figure 3:
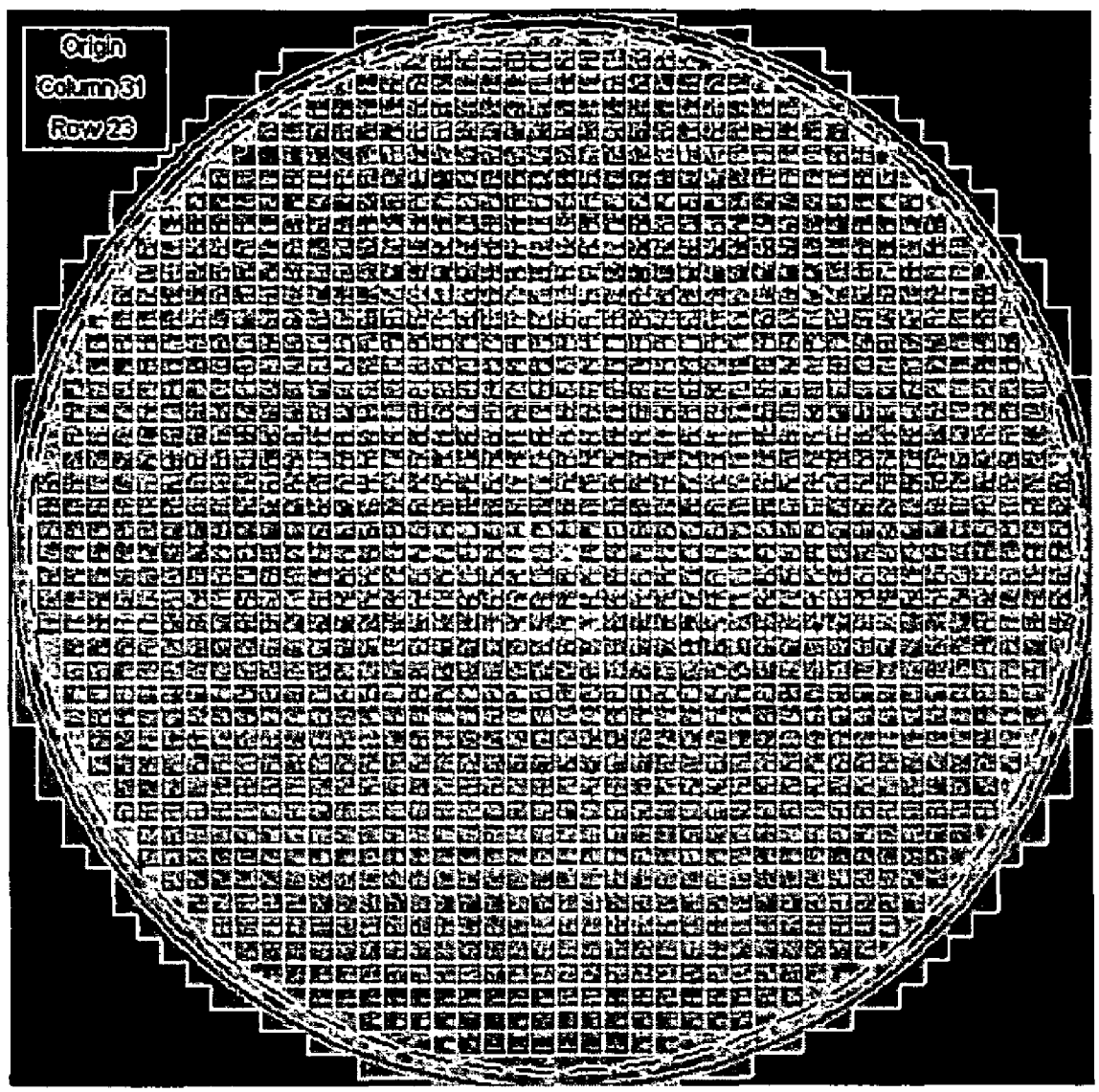
FIG. 3 is an example of an optic image map for a wafer.

These optic images may be collected and made into a form of data for a particular part of the wafer as in the method described above or for the entire wafer. The important point in the present invention is to obtain an optic image data corresponding to the location of the thickness data. The optic image data obtained are stored in analog or digital type. Various oxide layers used in semiconductor have unique colors corresponding to the thickness of sub-layer and the oxide layers so that the optic image is converted into analog or digital signal using the unique color and stored in a memory. FIG. 3 illustrates an optic image map for a wafer. An optic image recognized by the equipment is shown according to the thickness of the oxide layer for the entire wafer after STI CMP. The optic image means an individual image photo for the wafer through an optic microscope, for example.

The thickness data and the optic image obtained from the above method are matched and made into a library. Each optic image for the region represented by each thickness data is determined and the data conversion to analog or digital according to the signal processing of the optic image is accomplished. Consequently, a continuous image library for each thickness can be constructed.

The methods for matching and making a library of the thickness data and the optic image may be various: a method of acquiring the thickness and optic image data by splitting each region of the wafer with a specific size; a method of acquiring the thickness and optic image data according to X/Y coordinates of the wafer using the database including the size of a chip in the wafer; a method of acquiring the optic image data for the location previously set as the point for measuring the thickness; and a method of acquiring the thickness and optic image data by matching the optic image for several particular regions of the wafer with the thickness data.

Thus, the method of inspecting an insulating layer by using the thickness and the library of optic images in the present invention can considerably improve the conventional methods that depend only on the thickness or the optic images by making the thickness and the optic image for the part or whole of the wafer into a form of data, matching them, and making a library of them. Because the lack of wafer representative due to the restriction of monitoring pattern is overcome and the wafer representative is improved, monitoring the process and measuring the global planarization for wafer unit can be more accurate.

The foregoing embodiments are merely exemplary and are not to be construed as limiting the present invention. The present teachings can be readily applied to other types of apparatuses. The description of the present invention is intended to be illustrative, and not to limit the scope of the claims. Many alternatives, modifications, and variations will be obvious to those skilled in the art.

What is claimed is:

1. A method for inspecting an insulating layer deposited or planarized on a substrate in fabrication processes of semiconductor with a library of optical images, the method comprising:

measuring a thickness of the insulating layer;

collecting an optical image of the insulating layer corresponding to a location of the measured thickness data, and transforming the optical image into optical image analog data or optical image digital data;

creating a library by matching the measured thickness data and the optical image data collected on the same location on the substrate; and identifying defects in the insulating layer based on the library.

2. The method as defined by claim 1, wherein the thickness data is data for a particular region or the whole of a wafer.

3. The method as defined by claim 1, wherein the data for the optical image is data for a particular region or the whole of a wafer.

4. The method as defined by claim 1, wherein the optical image is stored as an analog or digital image.

5. The method as defined by claim 1, wherein creating the library is such that each optical image for a region represented by each thickness data is determined and a continuous image library for each thickness is constructed.

6. A method for inspecting an insulating layer deposited or planarized on a substrate in fabrication processes of semiconductor with a library of optical images, the method comprising:

measuring a thickness of the insulating layer at a plurality of locations on the substrate;

collecting an optical image of the insulating layer for each of said plurality of locations on the substrate, and storing the optical image transformed into analog data or digital data;

correlating the optical image to the measured thickness of the insulating layer for each of said plurality of locations;

creating a library by matching the optical image to the thickness of the insulating layer for each of said plurality of locations; and identifying defects in the insulating layer based on the library.

* * * * *